United States Patent
Finnern et al.

(10) Patent No.: US 7,625,561 B2
(45) Date of Patent: Dec. 1, 2009

(54) **DIABODY WHICH SPECIFICALLY BINDS *STREPTOCOCCUS* SURFACE ANTIGEN I/II AND METHODS OF USE THEREOF**

(75) Inventors: Ricarda Finnern, Aachen (DE); Rainer Fischer, Monschau (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 143 days.

(21) Appl. No.: 11/578,641

(22) PCT Filed: Apr. 21, 2005

(86) PCT No.: PCT/EP2005/004284

§ 371 (c)(1),
(2), (4) Date: Mar. 20, 2007

(87) PCT Pub. No.: WO2005/103085

PCT Pub. Date: Nov. 3, 2005

(65) Prior Publication Data

US 2007/0231321 A1 Oct. 4, 2007

Related U.S. Application Data

(60) Provisional application No. 60/564,396, filed on Apr. 22, 2004.

(51) Int. Cl.
*A61K 39/42* (2006.01)
(52) U.S. Cl. .............. 424/165.1; 424/133.1; 424/136.1; 424/164.1; 530/387.1; 530/387.3; 530/388.2; 530/388.4
(58) Field of Classification Search ........................ None
See application file for complete search history.

(56) References Cited

U.S. PATENT DOCUMENTS

2002/0078472 A1* 6/2002 Christou et al. ............. 800/278

FOREIGN PATENT DOCUMENTS

WO    WO 88/06455    9/1988

OTHER PUBLICATIONS

Holliger et al (PNAS 90: 6444-6448), 1993.*
Holliger et al (Cancer Immunol Immunother 197 45:128-130), 1997.*
Colman et al. Research in Immunology 145: 33-36, 1994.*
Beiboer et al., "Guided Selection of a Pan Carcinoma Specific Antibody reveals Similar Binding Characteristics yet Structural Divergence Between the Original Murine Antibody and its Human Equivalent" J. Mol. Biol. 2000 296:833-849.
Kupper et al., "Generation of human antibody fragments against *Streptococcus mutans* using a phage display chain shuffling approach", BMC Biotechnology 2005 5(4):1-12.
Little et al., "Of mice and men:hybridoma and recombinant antibodies", Immunology Today 2000 21(8):364-370.
Ma et al., "An Investigation into the Mechanism of Protection by Local Passive Immunization with Monoclonal Antibodies against *Streptococcus mutans*", Infection and Immunity 1990 58(10):3407-3414.

* cited by examiner

*Primary Examiner*—David J Blanchard
*Assistant Examiner*—Oluwatosin Ogunbiyi
(74) *Attorney, Agent, or Firm*—Licata & Tyrrell P.C.

(57) ABSTRACT

Common oral diseases such as periodontitis and dental caries can be prevented effectively by passive immunization. The present invention provides human single chain Fv (scFv) and diabody antibody fragments based on the binding characteristics of the murine monoclonal antibody Guy's 13. Like the parent antibody, these derivatives bind specifically to SAI/II, the surface adhesin of *Streptococcus* and the human diabody derivative is capable of aggregating streptococcal cells, making it a useful candidate therapeutic agent for passive immunization against oral diseases.

2 Claims, 2 Drawing Sheets

FIG. 2

| scFv | FR1 | CDR1 | FR2 | CDR2 |
|---|---|---|---|---|
| MuV$_H$Guy13 | QVKLQESGPDLVKPGASVKISCKASGYTFT | DYNIH........ | WVKQSRGKSLEWIG | YIYPYNGNTYYNQKFKN |
| MuV$_L$Guy13 | DIELTQSPAIMSASPGEKVTITC....... | SASSSVSYMH.. | WFQQKPGTSPKLWLY | STSNLAS........ |
| HuV$_H$B10 | QVQLQESGAEVKKPGSSVKVSCKASGGTFS | RYALS........ | WVRQAPGQGLEWMG | GIIPIFGTTNYAQKFQG |
| HuV$_L$B10 | DIQMTQSPSSLSASVGDRVTITC....... | RASQGISNYLA. | WFQQKPGKAPKSLIY | AASSLQS........ |
| HuV$_H$D12 | QVQLQESGAEVKKPGESLKISCKGSGYSFT | SYWIG........ | WVRQMPGKGLEWMG | IIYPGDSDTRYSPSFQG |
| HuV$_L$D12 | DIQMTQSPSTLSASIGDRVTITC....... | RASEGIYHWLA. | WYQQKPGKAPKLLIY | EASRLQS........ |
| HuV$_H$H6 | QVQLQESGGGVVQPGRSLRLSCAASGFTFS | SYAMH........ | WVRQAPGKGLEWVS | YISSSGSTIYYADSVKG |
| HuV$_L$H6 | DIVMTQSPSSLSASVGDRVTITC....... | RASQGISNYLA. | WFQQKPGKAPKSLIY | AASSLQS........ |

| scFv | FR3 | CDR3 | FR4 | |
|---|---|---|---|---|
| MuV$_H$Guy13 | KATLTVDNSSTSAYMELRSLTSEDSAVYYCAT | YFDY................... | WGQGTTVTVS | (SEQ ID NO:1) |
| MuV$_L$Guy13 | GVPARFSGSGSGTSYSLTISRMEAEDAATYYC | HQRTSYPYT............. | FGGGTKLEIKRAAAEQKLISEEDLNGAA | (SEQ ID NO:2) |
| HuV$_H$B10 | RVTIAADESTSTAYLELSSLRSEDTALYYCAK | SYDYVWGSYRPNEYGLDI | WGQGTMVTVS | (SEQ ID NO:3) |
| HuV$_L$B10 | GVPSKFSGSGSGTEFTLTISSLQPEDFATYYC | QELISYPLT............ | FGGGTKLEIKRAAAEQKLISEEDLNGAA | (SEQ ID NO:4) |
| HuV$_H$D12 | QVTISADKSISTAYLQWSSLKASDTAMYYCAR | LGLQDDYVWGSPNWEDP | WGQGTLVTVS | (SEQ ID NO:5) |
| HuV$_L$D12 | GVPSRFSGSGSGTEFTLTISSLQPDDFATYYC | IQDFTYPRT............ | FGGGTKLEIKRAAAEQKLISEEDLNGAA | (SEQ ID NO:6) |
| HuV$_H$H6 | RFTISRDNAKNSLYLQMNRLRAEDTAVYYCAR | DMAGTSYYYYYMDV...... | WGKGTLVTVS | (SEQ ID NO:7) |
| HuV$_L$H6 | GVPSKFSGSGSGTEFTLTISSLQPEDFATYYC | QELISYPLT............ | FGGGTKLEIKRAAAEQKLISEEDLNGAA | (SEQ ID NO:8) |

SEQUENCE LISTING

<160> NUMBER OF SEQ ID NOS: 23

<210> SEQ ID NO 1
<211> LENGTH: 112
<212> TYPE: PRT
<213> ORGANISM: Mus musculus

<400> SEQUENCE: 1

Gln Val Lys Leu Gln Glu Ser Gly Pro Asp Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Ile His Trp Val Lys Gln Ser Arg Gly Lys Ser Leu Glu Trp Ile
            35                  40                  45

Gly Tyr Ile Tyr Pro Tyr Asn Gly Asn Thr Tyr Tyr Asn Gln Lys Phe
        50                  55                  60

Lys Asn Lys Ala Thr Leu Thr Val Asp Asn Ser Ser Thr Ser Ala Tyr
65                  70                  75                  80

Met Glu Leu Arg Ser Leu Thr Ser Glu Asp Ser Ala Val Tyr Tyr Cys
                85                  90                  95

Ala Thr Tyr Phe Asp Tyr Trp Gly Gln Gly Thr Thr Val Thr Val Ser
            100                 105                 110

<210> SEQ ID NO 2
<211> LENGTH: 124
<212> TYPE: PRT
<213> ORGANISM: Mus musculus

<400> SEQUENCE: 2

Asp Ile Glu Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Leu Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Thr Ser Tyr Pro Tyr Thr
                85                  90                  95

Phe Gly Gly Gly Thr Lys Leu Glu Ile Lys Arg Ala Ala Ala Glu Gln
            100                 105                 110

Lys Leu Ile Ser Glu Glu Asp Leu Asn Gly Ala Ala
            115                 120

<210> SEQ ID NO 3
<211> LENGTH: 126
<212> TYPE: PRT
<213> ORGANISM: Artificial Sequence
<220> FEATURE:
<223> OTHER INFORMATION: Synthetic diabody heavy chain variable domain

<400> SEQUENCE: 3

Gln Val Gln Leu Gln Glu Ser Gly Ala Glu Val Lys Lys Pro Gly Ser
1               5                   10                  15

Ser Val Lys Val Ser Cys Lys Ala Ser Gly Gly Thr Phe Ser Arg Tyr

-continued

```
                    20                  25                  30

Ala Leu Ser Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Lys Phe
    50                  55                  60

Gln Gly Arg Val Thr Ile Ala Ala Asp Glu Ser Thr Ser Thr Ala Tyr
65                  70                  75                  80

Leu Glu Leu Ser Ser Leu Arg Ser Glu Asp Thr Ala Leu Tyr Tyr Cys
                85                  90                  95

Ala Lys Ser Tyr Asp Tyr Val Trp Gly Ser Tyr Arg Pro Asn Glu Tyr
            100                 105                 110

Gly Leu Asp Ile Trp Gly Gln Gly Thr Met Val Thr Val Ser
        115                 120                 125

<210> SEQ ID NO 4
<211> LENGTH: 125
<212> TYPE: PRT
<213> ORGANISM: Artificial Sequence
<220> FEATURE:
<223> OTHER INFORMATION: Synthetic diabody light chain variable domain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Glu Leu Ile Ser Tyr Pro Leu
                85                  90                  95

Thr Phe Gly Gly Gly Thr Lys Leu Glu Ile Lys Arg Ala Ala Ala Glu
            100                 105                 110

Gln Lys Leu Ile Ser Glu Glu Asp Leu Asn Gly Ala Ala
        115                 120                 125

<210> SEQ ID NO 5
<211> LENGTH: 125
<212> TYPE: PRT
<213> ORGANISM: Artificial Sequence
<220> FEATURE:
<223> OTHER INFORMATION: Synthetic diabody heavy chain variable domain

<400> SEQUENCE: 5

Gln Val Gln Leu Gln Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Leu Gly Leu Gln Asp Asp Tyr Val Trp Gly Ser Pro Asn Trp
            100                 105                 110

Phe Asp Pro Trp Gly Gln Gly Thr Leu Val Thr Val Ser
        115                 120                 125

<210> SEQ ID NO 6
<211> LENGTH: 125
<212> TYPE: PRT
<213> ORGANISM: Artificial Sequence
<220> FEATURE:
<223> OTHER INFORMATION: Synthetic diabody light chain variable domain

<400> SEQUENCE: 6

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Glu Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gln Asp Phe Thr Tyr Pro Arg
                85                  90                  95

Thr Phe Gly Gln Gly Thr Lys Leu Glu Ile Lys Arg Ala Ala Ala Glu
            100                 105                 110

Gln Lys Leu Ile Ser Glu Glu Asp Leu Asn Gly Ala Ala
        115                 120                 125

<210> SEQ ID NO 7
<211> LENGTH: 122
<212> TYPE: PRT
<213> ORGANISM: Artificial Sequence
<220> FEATURE:
<223> OTHER INFORMATION: Synthetic diabody heavy chain variable domain

<400> SEQUENCE: 7

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Val Tyr Tyr Cys
                85                  90                  95

Ala Arg Asp Met Ala Gly Thr Ser Tyr Tyr Tyr Tyr Met Asp Val
            100                 105                 110

Trp Gly Lys Gly Thr Leu Val Thr Val Ser
        115                 120

<210> SEQ ID NO 8
```

```
<211> LENGTH: 125
<212> TYPE: PRT
<213> ORGANISM: Artificial Sequence
<220> FEATURE:
<223> OTHER INFORMATION: Synthetic diabody light chain variable domain

<400> SEQUENCE: 8

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Glu Leu Ile Ser Tyr Pro Leu
                85                  90                  95

Thr Phe Gly Gly Gly Thr Lys Leu Glu Ile Lys Arg Ala Ala Ala Glu
            100                 105                 110

Gln Lys Leu Ile Ser Glu Glu Asp Leu Asn Gly Ala Ala
        115                 120                 125

<210> SEQ ID NO 9
<211> LENGTH: 8
<212> TYPE: PRT
<213> ORGANISM: Artificial Sequence
<220> FEATURE:
<223> OTHER INFORMATION: Synthetic linker

<400> SEQUENCE: 9

Thr Gly Gly Gly Ser Ser Ala Leu
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic linker

<400> SEQUENCE: 10

Ser Val Asp Gly Gly Gly Gly Ser Val His
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Synthetic linker

<400> SEQUENCE: 11

Gly Gly Gly Gly Ser
1               5

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 12
caggaaacag ctatgac                                                      17

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 13
gaattttctg tatrggg                                                      17

<210> SEQ ID NO 14
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 14
tgagcacaca gtgcactcga catcgtgatg acccagtctc c                            41

<210> SEQ ID NO 15
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 15
tgagcacaca gtgcactcga catccagatg acccagtctc c                            41

<210> SEQ ID NO 16
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 16
gagtcattct cgacttgcgg ccgcacgttt gatytccasc ttggtcc                      47

<210> SEQ ID NO 17
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 17
gtcctcgcaa ctgcggccca gccggccatg gcccaggtgc agctgcrgag tcggg             55

<210> SEQ ID NO 18
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 18
gtcctcgcaa ctgcggccca gccggccatg gcccaggtac agctgcrcag tcagg             55

<210> SEQ ID NO 19
<211> LENGTH: 36
```

```
<212> TYPE: DNA
<213> ORGANISM: Artificial Sequence
<220> FEATURE:
<223> OTHER INFORMATION: Synthetic oligonucleotide

<400> SEQUENCE: 19
gagtcattct cgtgtcgaca cggtgaccat tgtccc                                 36

<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 20
gagtcattct cgtgtcgaca cagtgaccag ggtgcc                                 36

<210> SEQ ID NO 21
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 21
tgagcacaca gtgcactcga catcgagctc actcagtctc c                           41

<210> SEQ ID NO 22
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 22
ttttcctttt gcggccgccc gttttatttc caactttgt                              39

<210> SEQ ID NO 23
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 23
gagtcattct cgtgtcgaca cggtgaccgt ggtgccttgg ccccagtagt caaagtaggt       60
```

DIABODY WHICH SPECIFICALLY BINDS *STREPTOCOCCUS* SURFACE ANTIGEN I/II AND METHODS OF USE THEREOF

CROSS-REFERENCE TO RELATED APPLICATIONS

This application claims benefit of priority to PCT/EP2005/004284, filed Apr. 21, 2005 and U.S. Provisional Patent Application Ser. No. 60/564,396, files Apr. 22, 2004, whose contents are incorporated herein by reference in their entireties.

BACKGROUND OF THE INVENTION

Dental caries is the most common infectious disease of humans. The main causative agent is a group of streptococcal species collectively described as the mutans streptococci (Balakrishnan, et al. (2000) *Aust. Dent. J.* 45:235-45). *Streptococcus mutans* has been identified as the major etiological agent of the disease. Unlike many other diseases, dental caries is as prevalent in the West as it is in developing countries, and therefore attracts significant interest from medical and dental authorities as well as pharmaceutical companies. The first step in the initiation of infection is the attachment of the bacterium to a suitable receptor; an ideal point for intervention. Two groups of proteins from mutans streptococci represent primary candidates for a human caries vaccine: glucosyltransferase enzymes, which synthesize adhesive glycans and allow microbial accumulation; and cell surface fibrillar proteins that mediate adherence to the salivary pellicle (Hajishengallis and Michalek (1999) *Oral Microbiol. Immunol.* 14:1-20). The bacterial adhesin SAI/II (Russell, et al. (1978) *Arch. Oral Biol.* 23:7-15), a surface-displayed protein with a molecular mass of 190 kDa, plays an important role in the initial attachment of *Streptococcus mutans* to the tooth surface.

The murine monoclonal antibody Guy's 13 (Smith and Lehner (1989) *Oral Microbiol. Immunol.* 4:153-8) which specifically recognizes the SAI/II protein of *Streptococcus mutans* and *Streptococcus sobrinus* (Smith and Lehner (1989) supra) has been used successfully to prevent *Streptococcus mutans* colonization and the development of dental caries in non-human primates (Lehner, et al. (1985) *Infect. Immun.* 50:796-9). The antibody also prevented bacterial colonization in human clinical trials (Ma, et al. (1990) *Infect. Immun.* 58:3407-14; Ma, et al. (1989) *Clin. Exp. Immunol.* 77:331-7). However, like other murine antibodies, a major limitation in clinical applications may be the human anti-mouse antibody response (HAMA), which can increase the rate of clearance and initiate allergic reactions (Saleh, et al. (1990) *Cancer Immunol. Immunother.* 32:185-90). The problems associated with murine antibodies can be overcome by replacing murine sequences with their human counterparts, e.g., by chimerization (Mountain and Adair (1992) *Biotechnol. Genet. Eng. Rev.* 10:1-142), CDR grafting (Kettleborough, et al. (1991) *Protein Eng.* 4:773-83) and guided selection using phage display technology (Beiboer, et al. (2000) *J. Mol. Biol.* 296:833-49). Furthermore, the use of antibody fragments rather than whole antibodies also removes some of the constant regions that may provoke an immune response.

Anti-SAI/II antibodies and fragments thereof have been disclosed in U.S. Pat. Nos. 5,518,721; 5,612,031; and 5,854,402 and WO 88/06455. These disclosures teach combating dental caries using an anti-SAI/II antibody composition in the form of a toothpaste, mouthwash, chewing gum, lozenge or gel.

However, and despite the fact that several potential therapies to combat dental caries using an anti-SAI/II antibody have been taught, the production and existence of engineered human diabodies which overcome problems associated with conventional antibodies and which can efficiently be used to treat dental caries have not been identified.

SUMMARY OF THE INVENTION

The present invention provides an isolated diabody which specifically binds *Streptococcus* Surface Antigen I/II (SAI/II) wherein the diabody is composed of a human heavy chain variable domain and a human light chain variable domain. In one embodiment, the heavy chain variable domain has an amino acid sequence of SEQ ID NO:3, SEQ ID NO:5, or SEQ ID NO:7. In another embodiment, the light chain variable domain has an amino acid sequence of SEQ ID NO:4, SEQ ID NO:6, or SEQ ID NO:8. In particular embodiments, the diabody contains a short linker sequence located between the heavy chain variable domain and light chain variable domain and is of the sequence represented in SEQ ID NO:9.

A vector containing a nucleic acid sequence encoding a diabody which specifically binds *Streptococcus* SAI/II and a host cell containing and capable of expressing the same are further embodiments of the present invention.

Another embodiment of the present invention is a method for preventing or treating an oral disease associated with a *Streptococcus*. The method involves administering an effective amount of a diabody which specifically binds *Streptococcus* SAI/II so that at least one sign or symptom of an oral disease is prevented or treated.

Compositions and kits containing a diabody which specifically binds *Streptococcus* SAI/II are also provided.

BRIEF DESCRIPTION OF THE DRAWINGS

FIG. 2 shows the amino acid sequences of the human scFv antibody fragments.

DETAILED DESCRIPTION OF THE INVENTION

Antibodies recognizing the oral pathogen *Streptococcus mutans* provide a novel approach for the control and prevention of dental caries. A monoclonal antibody that binds specifically to the SAI/II surface adhesin of *Streptococcus mutans* has been isolated (Saleh, et al. (1990) supra) and has been expressed in plants as a secretory IgA (sIgA) (Ma, et al. (1998) *Nat. Med.* 4:601-6). In Phase II clinical trials, this recombinant antibody has been shown to prevent recolonization of the mouth by *Streptococcus mutans* when coated onto the teeth and gums after initial bacterial eradication. sIgA is an appropriate format for the topical application of antibodies that inhibit the colonization of the tooth surface by *Streptococcus mutans* because this is the predominant form of antibody naturally found in the saliva. However, each sIgA comprises ten polypeptide chains of four different types making it difficult to produce on a large scale in conventional production systems.

As an alternative, a human diabody derivative of the murine Guy's 13 antibody has now been generated using a chain shuffling approach based on human antibody variable gene phage-display libraries. The human antibody fragments were expressed in bacteria as scFv and diabody derivatives and used to aggregate *Streptococcus mutans* in vitro. The diabodies were able to aggregate the bacteria and therefore are useful as therapeutic agents to treat or prevent dental caries.

The diabody derivatives of the present invention are advantageously useful over other antibody and antibody fragments known in the art because they are easy to express in large quantities, can penetrate tissues easily and lack the constant domains that promote often unwanted and usually superfluous effector functions. Further, because the diabodies of the invention are not of murine origin, they do not provoke an immune reaction in the human host, leading to rapid clearance and poor efficacy during long-term treatment. Since dental caries tend to be chronic rather than acute, murine antibodies are of little benefit to patients in the long-term. While scFvs to SAI/II have been produced (Ma, et al. (1990) supra), there are two drawbacks of scFvs compared to the ideal sIgA format, monovalency and instability. ScFvs are monovalent because the heavy and light chains are joined by a flexible peptide linker, which allows the two domains to fold and interact with each other. By using diabodies, wherein the linking peptide is shortened thereby forcing the heavy and light chain variable domains to interact to form a dimer, the drawback of using scFvs is overcome. Further, as a consequence of this interaction, the diabody is bivalent like the parent immunoglobulin, and therefore has increased binding avidity.

Figure 1:
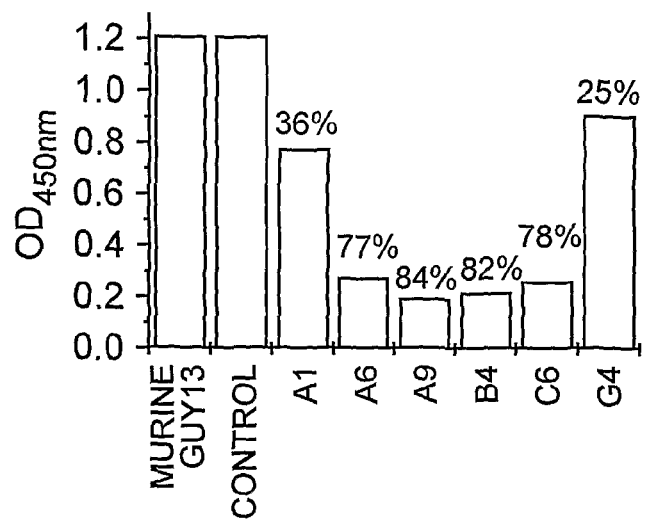
FIG. 1 shows the inhibition of binding of chimeric scFv (mGuy13VH/huVL; A1, A6, A9, B4, C6, and G4) to SAI/II by the monoclonal Ab Guy13.

By way of illustration, human scFv antibody fragments based on the murine monoclonal antibody Guy's 13 were constructed using two consecutive rounds of variable-domain shuffling and phage-library selection. First, a chimeric scFv was generated by amplifying the murine Guy's 13 heavy chain variable region, and inserting it into a human light chain variable region phage display library. The resulting phage display library had a complexity of $5 \times 10^5$. Single chain Fv antibody fragments with appropriate binding activities were selected on purified, immobilized SAI/II antigen. Three rounds of selection were carried out and unique candidate antibodies were identified by ELISA. Subsequent sequencing yielded five antibody fragments (chimscFvA1, chimscFvA6, chimscFvA9, chimscFvB4, and chimscFvG4). Sequencing of the human variable genes showed that two of the clones, chimscFvA6 and chimscFvB4, belonged to family Vκ1 with clone chimscFvA6 being homologous to HK137 and clone chimscFvB4 being homologous to the L12 germline gene family. ChimscFvA9 belonged to family Vκ4 DPk24. ChimscFvA1 and chimscFvG4 belonged to family Vλ3 DPL16). Inhibition ELISA showed that the binding of all six chimeric scFvs to SAT/II could be inhibited by the Guy's 13 murine monoclonal antibody. The binding of chimeric scFvs A6, A9, B4 and C6 was inhibited by approximately 80%, indicating that epitope recognition was maintained (FIG. 1). The binding of the chimeric scFvs A1 and G4 was only inhibited by approximately 30%, indicating that these antibodies recognized a different epitope.

Figure 3:
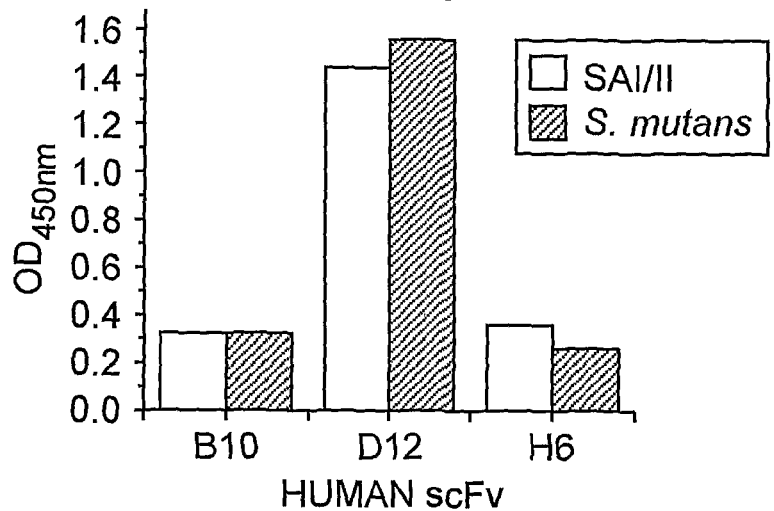
FIG. 3 shows human scFv binding (B10, D12, and H6) to SAI/II and *Streptococcus mutans*.

The selected human $V_L$ genes were introduced into a human $V_H$ library (complexity $8 \times 10^8$) and a combinatorial library with a complexity of $1 \times 10^6$ was established. Three rounds of selection were carried out in solution using SAI/II antigen coupled to paramagnetic beads. Eleven human scFvs were identified by ELISA. Subsequent sequence analysis identified three human scFvs, clones huscFv B10, huscFv D12 and huscFv H6. FIG. 2 shows the amino acid sequences of the human scFv antibody fragments. The human $V_L$ domain in chimeric scFv A6 (Vκ1 HK137) was selected in combination with two different human variable heavy chains to yield human scFvs B10 and H6, respectively. The $V_H$ domain of human scFv B10 (SEQ ID NO:3) is homologous to $V_H1$ family DP10, and the $V_H$ domain of human scFv H6 (SEQ ID NO:7) is homologous to $V_H3$ family DP35. The human $V_L$ domain in chimeric scFv B4 (Vκ1 L12) (SEQ ID NO:6) was selected in combination with one human variable heavy chain giving the human scFv D12. The $V_H$ domain of human scFv D12 (SEQ ID NO:5) is homologous to $V_H5$ family DP73. FIG. 3 shows the binding of the three human scFvs to the SAI/II antigen and the pathogenic bacterium *Streptococcus mutans*. Inhibition ELISA showed that the binding of all three human scFvs to SAI/II was inhibited by Guy's 13, indicating that epitope recognition was maintained.

Figure 4:
FIG. 4 shows human diabodies (B10, D12, and H6) binding to SAI/II and *Streptococcus mutans*.

Recombinant antibody fragments can be engineered to assemble into stable multimeric oligomers of high binding avidity and specificity (Kortt, et al. (2001) *Biomol. Eng.* 18:95-108). A scFv molecule joined by a linker of 3-12 residues cannot fold into a functional Fv domain and instead associates with a second scFv molecule to form a bivalent dimer (diabody, approx. 60 kDa). For the cross-linking of cell surface antigens at least two binding moieties are necessary. The diabody is the smallest bivalent antibody molecule able to fulfill this requisite. Human diabodies were constructed by PCR amplifying (Table 2) the variable heavy and light chain genes from human scFvs B10, D12 and H6 and murine scFv Guy's 13 and inserting the amplicons in two consecutive steps into the vector pHenIXdia, containing a 10 amino acid residue linker. The integrity of the clones was confirmed by sequencing and the binding activity was demonstrated by ELISA using both the SAI/II antigen and *Streptococcus mutans* cells (FIG. 4). Because the F(ab')$_2$ derivative, and not the monovalent Fab fragment, was protective against dental caries, the bivalent binding of the murine Guy's 13 is required for protection (Ma, et al. (1990) supra). *Streptococcus mutans* became aggregated in a dose-dependent manner when grown in the presence of mouse diabody Guy's 13 and human diabody D12, however, the human diabodies significantly outperformed Guy's 13 at similar concentrations. Therefore, there did not appear to be a significant loss in binding affinity in the generation of human diabodies which binds Streptococcal SAI/II.

Accordingly, the present invention relates to a diabody containing the human variable domain of the monoclonal antibody Guy's 13, wherein said diabody specifically binds Streptococcal SAI/II and facilitates aggregation of Streptococcal cells. A diabody which binds Streptococcal SAI/II is an engineered antibody which physically interacts with SAI/II, particularly from *Streptococcus mutans* and *Streptococcus sobrinus*, to block the adhesin function of SAI/II thereby preventing Streptococcal colonization in a host. As the diabody of the present invention is derived from the variable domain of Guy's 13, it is contemplated that said diabody will be useful in preventing the colonization of *Streptococcus mutans* and *Streptococcus sobrinus*.

As used herein, the term diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function as described in detail by Holliger et al. (1993) *Proc. Natl. Acad. Sci. USA* 90:6444 and reviewed by Poljak (1994) *Structure* 2:1121-1123. This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) *Biotechnology* 14:192-196, and U.S. Pat. No. 6,492,123, herein incorporated by reference, can be used. Once generated, the binding specificity can be determined by, for example, equilibrium methods (e.g., enzyme-linked immunoabsorbent assay (ELISA) or radioimmunoassay (RIA)), or kinetics (e.g. BIACORE™ analysis). Alternatively, the diabody can be subjected to other biological activity assays, e.g., bacterial aggregation or cologonization assays, in order to evaluate its potency or pharmacological activity and potential efficacy as a therapeutic agent. Such assays are disclosed herein and are well-known in the art.

The generation of diabodies containing the human variable domains is described further in the Examples section of the present application.

It should be clear that the diabodies described herein are not limited to recognizing the same epitope as monoclonal antibody Guy's 13 but may also comprise variable domains of other anti-SAI/II antibodies, such as the anti-SAI/II antibodies described in U.S. Pat. Nos. 5,518,721; 5,612,031; and 5,854,402 and WO 88/06455.

While a diabody of the present invention specifically binds SAI/II, as one of skill in the art can appreciate, a diabody can also contain two scFv's of different specificities. For example, a diabody of the invention can simultaneously bind SAI/II on the one hand and may target another molecule, such as an adhesive glycan or any other molecule, on the other hand.

In one embodiment of the present invention, a diabody which binds SAI/II is a diabody designated D12 which contains a human heavy chain variable domain of SEQ ID NO:5 and a light chain variable domain of SEQ ID NO:6 (FIG. 2). In another embodiment, a diabody which binds SAI/II is a diabody designated B10 which contains a human heavy chain variable domain of SEQ ID NO:3 and a light chain variable domain of SEQ ID NO:4. In a further embodiment, a diabody which binds SAI/II is a diabody designated H6 which contains a human heavy chain variable domain of SEQ ID NO:7 and a light chain variable domain of SEQ ID NO:8.

In particular embodiments, the heavy and light variable chains domains of the diabody of the invention are joined or operably linked by a linker sequence. The linker can be short peptide of too few amino acids to allow the $V_L$ domain of a chain to combine with the $V_H$ domain of that chain. This can be less than 10 amino acids, e.g., 5, 4, 3, 2, or 1. It can be in certain cases that 9, 8, 7 or 6 amino acids are suitable. In some cases it may be "-1", i.e., with the $V_H$ and $V_L$ domains linked directly together, but with one of them missing an amino acid. In certain cases, the omission of more than one amino acid from one or both of the domains may be feasible. Suitable linkers for use in a diabody of the present invention include, but are not limited to, Thr-Gly-Gly-Gly-Ser-Ser-Ala-Leu (SEQ ID NO:9); Ser-Val-Asp-Gly-Gly-Gly-Gly-Ser-Val-His (SEQ ID NO:10); Gly-Gly-Gly-Gly-Ser (SEQ ID NO:11); and linkers disclosed in U.S. Pat. No. 6,492,123.

The present invention also includes vectors and host cells containing nucleic acid sequences encoding a diabody of the present invention.

For recombinant production of a diabody, the nucleic acid sequences encoding the diabody are isolated and inserted into a replicable vector for further cloning (amplification of the DNA) or for expression. Nucleic acid sequences encoding a diabody of the present invention are readily isolated and sequenced using conventional procedures (e.g., by using oligonucleotide probes such as those disclosed herein that are capable of binding specifically to genes encoding the heavy and light chains of the SAI/II diabody). Many vectors are available. The vector components generally include, but are not limited to, one or more of the following: a signal sequence, an origin of replication, one or more marker genes, an enhancer element, a promoter, and a transcription termination sequence.

The diabody of this invention can be produced recombinantly not only directly, but also as a fusion polypeptide with a heterologous polypeptide, which is a signal sequence or other polypeptide having a specific cleavage site at the N-terminus of the mature protein or polypeptide. The heterologous signal sequence selected is generally one that is recognized and processed (i.e., cleaved by a signal peptidase) by the host cell. For prokaryotic host cells, the signal sequence can include, for example, alkaline phosphatase, penicillinase, lpp, or heat-stable enterotoxin II leaders. For yeast secretion, leader sequences from yeast invertase, alpha-factor (including *Saccharomyces* and *Kluyveromyces* alpha-factor leaders), or acid phosphatase, the *C. albicans* glucoamylase leader, or the signal described in WO 90/13646. In mammalian cell expression, mammalian signal sequences as well as viral secretory leaders, for example, the herpes simplex gD signal, are available. The nucleic acid sequences for such precursor amino acid sequences are ligated in reading frame to nucleic acid sequences encoding the diabody.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well-known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors can also contain a selection gene, also termed a selectable marker. Typical selection genes encode proteins that confer resistance to antibiotics or other toxins, e.g., ampicillin, neomycin, methotrexate, or tetracycline; complement auxotrophic deficiencies; or supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the diabody nucleic acid sequences, such as DHFR, thymidine kinase, metallothionein-I and -II, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with nucleic acid sequences encoding a diabody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb, et al. (1979) *Nature* 282:39). The trp1 gene provides a selection marker for a mutant strain of yeast lacking the ability to grow in tryptophan, for example, ATCC No. 44076 or PEP4-1 (Jones (1977) *Genetics* 85:12). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis* (Van den Berg (1990) *Bio/Technology* 8:135). Stable multi-copy expression vectors for secretion of mature recombinant human serum albumin by industrial strains of *Kluyveromyces* have also been disclosed (see, e.g., Fleer, et al. (1991) *Bio/Technology* 9:968-975).

Expression and cloning vectors usually contain a promoter that is recognized by the host organism and is operably linked to the diabody nucleic acid sequence. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno sequence operably linked to the DNA encoding the diabody.

Promoter sequences are known for eukaryotes. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phos-phate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock romoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the rous sarcoma virus long terminal repeat can be used as the promoter.

Transcription of a DNA encoding the diabody of this invention by higher eukaryotes is often increased by inserting an enhancer sequence into the vector. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) *Nature* 297:17-18 on enhancing elements for activation of eukaryotic promoters. The enhancer can be spliced into the vector at a position 5' or 3' to the diabody-encoding sequence, but is generally located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

It is also contemplated that the diabody of the present invention can be expressed and isolated from plants. In plant cells, expression systems are often derived from recombinant Ti and Ri plasmid vector systems. In the cointegrate class of shuttle vectors, the gene of interest is inserted by genetic recombination into a non-oncogenic Ti plasmid that contains both the cis-acting and trans-acting elements required for plant transformation. Exemplary vectors include the pMLJ1 shuttle vector (DeBlock, et al. (1984) *EMBO J.* 3:1681-1689) and the non-oncogenic Ti plasmid pGV2850 (Zambryski, et al. (1983) *EMBO J.* 2:2143-2150). In the binary system, the gene of interest is inserted into a shuttle vector containing the cis-acting elements required for plant transformation. The other necessary functions are provided in trans by the non-oncogenic Ti plasmid. Exemplary vectors include the pBIN19 shuttle vector (Bevan (1984) *Nucl. Acids Res.* 12:8711-8721) and the non-oncogenic Ti plasmid pAL4404 (Hoekema, et al. (1983) *Nature* 303:179-180).

Promoters used in plant expression systems are typically derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV).

Suitable host cells for cloning or expressing the diabody nucleic acid sequences in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia* (e.g., *E. coli*), *Enterobacter, Erwinia, Klebsiella, Proteus, Salmonella* (e.g., *Salmonella typhimurium*), *Serratia* (e.g., *Serratia marcescans*), and *Shigella*, as well as Bacilli such as *B. subtilis* and

*B. licheniformis* (e.g., *B. licheniformis* 41P disclosed in DD 266,710), *Pseudomonas* such as *P. aeruginosa*, and *Streptomyces*. An exemplary *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for diabody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of diabodies in multicellular organisms include invertebrate cells such as plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV.

Plant and plant cell cultures of cotton, corn, potato, soybean, petunia, tomato, and banana, tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham, et al. (1977) *J. Gen Virol.* 36:59); baby hamster kidney cells (BHK, ATCC CCL 10); Chinese hamster ovary cells/-DHFR(CHO, Urlaub, et al. (1980) *Proc. Natl. Acad. Sci. USA* 77:4216); mouse sertoli cells (TM4, Mather (1980) *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather, et al. (1982) *Annals NY Acad. Sci.* 383:44-68); MRC 5 cells; FS4 cells; and a human hepatoma line (Hep G2).

Host cells are transformed with the above-described expression or cloning vectors for diabody production and cultured in conventional nutrient media modified as appropriate for inducing promoters, selecting transformants, or amplifying the genes encoding the desired sequences.

The host cells used to produce the antibody variant of this invention may be cultured in a variety of media. Commercially available media such as Ham's F10 (Sigma, St. Louis, Mo.), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham, et al. (1979) *Meth. Enz.* 58:44; Barnes, et al. (1980) *Anal. Biochem.* 102: 255; U.S. Pat. Nos. 4,767,704; 4,657,866; 4,927,762; 4,560, 655; or 5,122,469; WO 90/03430; WO 87/00195; or U.S. Pat. No. RE 30,985 can be used as culture media for the host cells. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN), trace elements (defined as inorganic compounds usually present at final concentrations in the micromolar range), and glucose or an equivalent energy source. Any other necessary supplements can also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the diabody can be produced intracellularly, in the periplasmic space, or directly secreted into the medium. If the diabody is produced intracellularly, as a first step, the particulate debris, either host cells or lysed fragments, is removed, for example, by centrifugation or ultrafiltration. Carter, et al. (1992) *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the diabody is secreted into the medium, supernatants from such expression systems are generally first concentrated using a commercially available protein concentration filter, for example, an Amicon or Millipore Pellicon ultrafiltration unit. A protease inhibitor such as PMSF can be included in any of the foregoing steps to inhibit proteolysis and antibiotics can be included to prevent the growth of adventitious contaminants.

The diabody composition prepared from the cells can be purified using, for example, hydroxylapatite chromatography, gel electrophoresis, dialysis, or affinity chromatography. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE chromatography on an anion or cation exchange resin (such as a polyaspartic acid column), chromatofocusing, SDS-PAGE, and ammonium sulfate precipitation are also available.

The human diabody derivative disclosed herein is capable of aggregating *Streptococcus mutans*, making it a useful candidate therapeutic agent for passive immunization against oral diseases. Accordingly, therapeutic compositions or formulations of a diabody are a further embodiment of the present invention. A diabody of the present invention can be applied to the tooth in the mouth of the mammal by any convenient method. Numerous methods are available for the treatment of teeth with various materials for various purposes. If the treatment is to be carried out by a dental surgeon, then the diabody can be formulated to be conveniently applied by painting the surface of the tooth. If the diabody is to be self-applied, then the diabody can be included in a toothpaste, mouthwash, chewing gum, lozenge or gel and applied during the regular brushing, or the diabody can be formulated and packaged as a separate treatment and applied separately before, after, and/or in between regular brushing times. Methods of self-application from toothpastes etc., can result in applications being repeated perhaps daily while the use of lozenges can result in more frequent application of the diabody. Chewing gums and gels may be regarded, for this purpose, as providing a certain amount of sustained release of the diabody over a period of half-an-hour or more and indeed, if sustained release of the diabody is required, then appropriate formulations can be used that will result in slow release of antibody into the mouth from the formulation as a result of the temperature or saliva conditions, etc., found in the mouth. In certain instances, it may be desirable to provide a more formal prolonged contact of the diabody with the tooth surface and in such cases, appropriate dental trays or adhesive strips can be used that will cover the tooth coated with a diabody composition and prevent the diabody from being removed, e.g., by saliva, for a predetermined period. Formulations for therapeutic administration of a diabody of the invention can be prepared by mixing the diabody having the desired degree of purity with optional physiologically acceptable carriers, excipients or stabilizers in accordance with well-established methods (Remington: The Science and Practice of Pharmacy, Alfonso R. Gennaro, editor, 20th ed. Lippingcott Williams & Wilkins: Philadelphia, Pa., 2000). Acceptable carriers, excipients, or stabilizers are nontoxic to recipients at the dosages and concentrations employed, and include buffers such as phosphate, citrate, and other organic acids; antioxidants; preservatives; low molecular weight (less than about 10 residues) polypeptides; proteins, such as serum albumin, gelatin, or other immunoglobulins; hydrophilic polymers; amino acids; monosaccharides, disaccharides, and other carbohydrates including glucose, mannose, or dextrins; chelating agents such as EDTA; sugars; salt-forming counter-ions; metal complexes (e.g., Zn-protein complexes); and/or non-ionic surfactants such as TWEEN, PLURONICS or polyethylene glycol (PEG).

A diabody composition can also contain more than one active compound, either operably linked or not operably linked, as necessary for the particular indication being treated, particularly those with complementary activities that do not adversely affect each other. For example, it may be desirable to further provide an antibiotic in combination with or as part of a diabody composition of the invention. Such molecules are suitably present in combination in amounts that are effective for the purpose intended.

In another embodiment of the invention, the diabody disclosed herein can be operably linked to a therapeutic agent, e.g. glucose oxidase or a defensin (see, e.g., Maisetta, et al. (2003) *Antimicrob. Agents Chemother.* 47:3349-3351). As used herein, operably associated or operably linked means that the diabody and therapeutic agent are joined or conjugated together. In the case of a diabody and a therapeutic protein, they can be operably linked by being translated from the same contiguous mRNA sequence. Alternatively, the diabody and therapeutic agent can be covalently attached via a linker such as those disclosed herein. Further, a therapeutic agent such as an antibiotic can be attached to a Lysine side chain amino group of the diabody of the present invention via an amide bond.

A further embodiment of the present invention is a method for preventing or treating an oral disease associated with a *Streptococcus* such as *Streptococcus mutans* and *Streptococcus sobrinus*. The method involves administering an effective amount of a diabody of the present invention to achieve improvement by inhibiting or reversing oral disease by improving or eliminating at least one sign or symptom (bacterial colonization) or other indicator of disease as determined by those skilled in the art. A diabody or diabody composition is administered and dosed in accordance with good medical practice, taking into account the clinical condition of the individual patient, the site and method of administration, scheduling of administration, patient age, sex, body weight and other factors known to medical practitioners.

Topical administration of a diabody is the most practical course for administration. It is important that the diabody be brought into contact with the surface of the tooth and ideally should be applied to all of the smooth and occlusal surfaces of the tooth.

In general, the exact amount of diabody that is applied does not appear to be critical since, in a method of this type, repeated application of diabody is not difficult and indeed, particularly after initial treatment by a dental surgeon, maintenance or top-up treatment can be carried out by the user at whatever frequency is desirable. By way of guidance, it can be indicated that somewhere of the order of 10 to 500 micrograms of diabody can be applied to each tooth on each occasion that diabody is applied but amounts of diabody outside this range can certainly be applied without causing detriment to the subject. The use of insufficient quantities of diabody simply means that the level of protection is not as great as would otherwise be obtainable while the use of excessive amounts of diabody does not improve the protection and simply results in unnecessary use of diabody.

The exact formulation for the diabody is not a matter of critical importance but depends entirely upon the method of application to be adopted and the convenience of the user. In all cases, it is important to formulate the diabody in an environment of appropriate pH and which is free from other deleterious materials which might bring about protein degradation and the formulation should, of course, also be free from microbial impurity that would be deleterious in the subject's mouth. For example, for use in the dental surgery, the diabody could be formulated as a simple aqueous dispersion containing somewhere in the region of 0.1 to 10 milligrams of diabody per 100 microliters of liquid and a liquid of such concentration could be applied to the tooth at the rate of about 1 to 10 microliters of dispersion per tooth. Where the diabody is to be formulated for self-administration, then the concentration can be selected bearing in mind the above guidelines, the quantities of the formulation that are normally taken on each occasion of self-administration and the fact that over administration of diabody will not be deleterious.

The diabody may also be useful in diagnostic assays, e.g., for detecting the presence of a Streptococcal cell expressing SAI/II in an dental caries.

For diagnostic applications, the diabody typically will be labeled with a detectable moiety. Numerous labels are available which can be generally grouped into the following categories: radioisotopes, fluorescent labels, or various enzyme-substrate labels.

Radioisotopes such as $^{35}S$, $^{14}C$, $^{125}I$, $^{3}H$, and $^{131}I$. The diabody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the diabody using the techniques disclosed in Current Protocols in Immunology, supra, for example. Fluorescence can be quantified using a fluorimeter.

Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzymology (ed J. Langone & H. Van Vunakis), Academic press, New York, 73:147-166 (1981).

Sometimes, the label is indirectly conjugated with the diabody. The skilled artisan will be aware of various techniques for achieving this. For example, the diabody can be conjugated with biotin and any of the three broad categories of labels mentioned above can be conjugated with avidin, or vice versa. Biotin binds selectively to avidin and thus, the label can be conjugated with the diabody in this indirect manner. Alternatively, to achieve indirect conjugation of the label with the diabody, the diabody is conjugated with a small hapten (e.g., digoxin) and one of the different types of labels mentioned above is conjugated with an anti-hapten antibody variant (e.g., anti-digoxin antibody). Thus, indirect conjugation of the label with the diabody can be achieved. The diabody can also be directly fused to, e.g., alkaline phosphatase as a recombinant protein.

In another embodiment of the invention, the diabody need not be labeled, and the presence thereof can be detected using a labeled antibody which binds to the diabody.

A diabody of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

As a matter of convenience, the diabody of the present invention can be provided in a kit, i.e., a packaged combination of reagents in predetermined amounts with instructions for performing the diagnostic assay. Where the diabody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The invention is described in greater detail by the following non-limiting examples.

EXAMPLE 1

Propagation of *Streptococcus mutans*

*Streptococcus mutans* 20523 serological group c was purchased from DSMZ (Braunschweig, Germany) and grown in an S2 containment laboratory in trypticase soy yeast extract medium (30 gram/L trypticase soy broth, 3 gram/L yeast extract, pH 7.0-7.2) at 37° C. for 2 days prior to use.

EXAMPLE 2

Cloning of spaP Gene

Nucleotides 214 to 3048 of the spaP gene (Bleiweis, et al. (1990) Arch. Oral Biol. 35 Suppl: 15S-23S), which encode the SAI/II antigen, were removed from pUC18 as a SfiI/NotI fragment and inserted into the bacterial expression vectors pCantab5E (Pharmacia, Freiburg, Germany) and psin1 (Amersdorfer and Marks (2000) *Methods Mol. Biol.* 145:219-40) which had been digested with the same enzymes. The pCantab5E vector contained an additional sequence encoding the E-tag, facilitating the detection of expressed proteins using the monoclonal antibody 5E (Pharmacia). The pSin1 vector similarly contained sequences encoding a MYC-tag, facilitating detection with the murine monoclonal antibody 9E10 (ATCC CRL 1729), and a His6 tag, allowing purification of expressed proteins by immobilized metal-chelate affinity chromatography (IMAC) and detection using a murine Penta-HIS antibody (Qiagen, Hilden, Germany). SAI/II expressed using psin1 was used for the selection of antibodies from phage-display libraries. SAI/II expressed in pCantab5E was used for enzyme-linked immunosorbent assays (ELISAs).

EXAMPLE 3

Coating Paramagnetic Beads with SAI/II

For the selection of phage-display antibodies, 250 µL of PBS-washed Dynabeads (Dynal Biotech GmbH, Hamburg, Germany) was resuspended in 500 µL 0.1 M phosphate buffer (pH 7.4) and mixed gently for 2 minutes. The beads were collected with a magnet, the supernatant discarded and the beads resuspended in 250 µL of the same buffer, followed by the addition of 500 µL SAI/II antigen. After incubation for 16 hours at 37° C. with slow tilt rotation, the beads were collected with a magnet and the supernatant was discarded. The coated beads were washed four times, twice with 0.13 M NaCl, 1% milk powder in 0.01 M phosphate buffer (pH 7.4) for 5 minutes at 4° C., once with 0.2 M Tris-HCl (pH 8.5) for 4 hours at 37° C. and again in the same buffer for 5 minutes at 4° C.

EXAMPLE 4

Cloning scFv Guy's 13 in pSin1

The variable region genes of the murine monoclonal antibody Guy's 13 were amplified using oligonucleotide primers LMB3 (5'-CAG GAA ACA GCT ATG AC-3'; SEQ ID NO:12) and fdSeq 1 (5'-GAA TTT TCT GTA TG/AG GG-3'; SEQ ID NO:13) followed by digestion with SfiI and NotI. The products were inserted into the phagemid vector pSin1, which had been treated with the same enzymes, and the recombinant vector was introduced into *E. coli* strain TG1.

EXAMPLE 5

Human SAI/II-Specific scFv Antibodies

The variable heavy chain antibody domain of the murine antibody Guy's 13 was cloned as an SfiI/SalI fragment in the bacterial expression vector pHenIX containing a light-chain antibody phage-display library derived from naïve human peripheral blood lymphocytes ($8 \times 10^8$). This vector is based on the phagemid vector pHen1 (Hoogenboom, et al. (1991) Nucl. Acids Res. 19:4133-7) designed to express antibody fragments as an N-terminal fusion with the minor coat protein of filamentous bacteriophage M13. An amber stop codon between the two fusion partners allows the expression of both soluble antibody fragments and phage particles displaying recombinant antibodies. The recombinant vectors were introduced into E. coli strain TG1. Three rounds of selection were carried out using immobilized SAI/II antigen in accordance with established methods (Marks, et al. (1991) J. Mol. Biol. 222:581-97). Elution was achieved using the monoclonal antibody Guy's 13 to select binders recognizing the same epitope. The expression of soluble scFvs was performed using standard methods. (Marks, et al. (1991) supra) and scFvs specific for the SAI/II antigen were identified by ELISA using SAI/II antigen. The selected variable antibody domain genes of the shuffled human light chains were cloned as ApaLI and NotI fragments in pHenIX containing a human variable heavy chain library ($8 \times 10^8$) and introduced into E. coli TG1. This was achieved by PCR amplification of the human light chain genes using primers Vκ4 ApaLI (5'-TGA GCA CAC AGT GCA CTC GAC ATC GTG ATG ACC CAG TCT CC-3'; SEQ ID NO:14), Vκ1 ApaLI (5'-TGA GCA CAC AGT GCA CTC GAC ATC CAG ATG ACC CAG TQT CC-3'; SEQ ID NO:15) and Jκ1 NotI (5'-GAG TCA TTC TCG ACT TGC GGC CGC ACG TTT GAT C/TTC CAC/G CTT GGT CCC-3'; SEQ ID NO:16). Three rounds of selection were carried out using SAI/II antigen immobilized on Dynabeads. Briefly, 150 μg of SAI/II-coated beads was blocked for 1 hour with 2 mL 2% milk powder. The beads were collected with a magnet, washed in PBS and incubated with the antibody phage display library for 1 hour on a turntable. The beads were washed 15 times with PBS/0.05% TWEEN 20 and 15 times with PBS to remove unbound phage. Bound phage were eluted with 100 μL 100 mM triethanolamine for 10 minutes on a turntable followed by neutralization in 200 μL 1 M Tris-HCl (pH 8.0). Eluted phage were used to infect exponentially growing E. coli TG1 and grown overnight at 30° C. on TYE plates containing 100 μg mL$^{-1}$ ampicillin, 1% glucose. Selection, phage rescue and induction of soluble scFv expression were carried out using standard methods (Marks, et al. (1991) supra). Antigen-specific human scFv fragments were identified by ELISA using the SAI/II antigen.

EXAMPLE 6

Propagation of Phage Display Antibody Libraries

One liter of 2×TY (supplemented with 100 μg mL$^{-1}$ ampicillin, 1% glucose) was inoculated with an aliquot of the phage antibody library glycerol stock. The rescue and induction of the phage was carried out essentially in accordance with established methods (Marks, et al. (1991) supra). Phagemid rescue was carried out by the addition of $10^{10}$ units of helper phage VCSM13 (Pharmacia) to the growing phage antibody library. The culture medium was changed to 2×TY containing 100μg/mL ampicillin and 25 μg/mL kanamycin and incubated on an orbital shaker overnight at 30° C. and 250 rpm. Phage were purified twice by PEG precipitation (20% PEG, 2.5 M NaCl) and resuspended in a final volume of 2 mL PBS. The phage were stored at 4° C. until further use.

EXAMPLE 7

DNA Sequencing

The number of unique clones was determined by PCR amplification of the recombinant antibody inserts using primers LMB3 (5'-CAG GAA ACA GCT ATG AC-3'; SEQ ID NO:12) and fdSeq 1 (5'-GAA TTT TCT GTA TG/AG G-3'; SEQ ID NO:13) followed by digestion with the restriction enzyme BstNI (New England Biolabs, Beverly, Mass.). The variable antibody genes from two clones of each restriction pattern were analyzed by PCR cycle sequencing using infrared labeled primers according to the manufacturer's instructions (LI-COR, Lincoln, Nebr.). Sequencing reactions were carried out on a LI-COR automated DNA sequencer (4000 L) and the sequences were analyzed using SEQUENCHER 3.1 (Gene Codes Corporation, Ann Arbor, Mich.). The sequences of the VH and VL genes were compared with the germline sequences in the V-BASE database (http://www.mrccpe.cam.ac.uk/vbase-ok.php?-menu=901; Tomlinson et al., MRC Centre for Protein Engineering, Cambridge, UK).

EXAMPLE 8

Construction of Diabodies

The construction of diabodies (Holliger, et al. (1993) Proc. Natl. Acad. Sci. USA 90:6444-8) was carried out by PCR amplification of the variable heavy and light chain antibody regions of the human scFv clones and subcloning these in vector pHenIXdia. The diabody constructs consisted of the variable heavy and light chain antibody domains linked by a ten-amino-acid linker (Thr-Gly-Gly-Gly-Ser-Ser-Ala-Leu; SEQ ID NO:9), forcing the expressed domains to attach to a complementary chain in solution to create two antigen-binding sites. The primers used for the construction of the diabody antibody format are listed in Table 1.

TABLE 1

| Template | $V_L$Amplification | |
|---|---|---|
| pHenIX Human scFv B10 | VK1 ApaLI | JK1 NotI |
| pHenIX Human scFv H6 | VK1 ApaLI | JK1 NotI |
| pHenIX Human scFv D12 | VK4 ApaLI | JK1 NotI |
| pHenIX scFv mGuy13 | mGuy13 ApaLI | mGuy13 NotI |
| | $V_H$Amplification | |
| pHenIX Human scFv B10 | $V_H$4 SfiI/NcoI | $J_H$3 for SalI |
| pHenIX Human scFv H6 | $V_H$6 SfiI/NcoI | $J_H$2 for SalI |
| pHenIX Human scFv D12 | $V_H$4 SfiI/NcoI | $J_H$2 for SalI |
| pHenIX scFv mGuy13 | $V_H$4 SfiI/NcoI | mGuy13 SalI | wherein,

Vκ1 ApaLI:
(SEQ ID NO:15)
5'-TGA GCA CAC AGT GCA CTC GAC ATC CAG ATG ACC CAG TCT CC-3';

Vκ4 ApaLI:
(SEQ ID NO:14)
5'-TGA GCA CAC AGT GCA CTC GAC ATC GTG ATG ACC CAG TCT CC-3';

Jκ1 NotI:
(SEQ ID NO:16)
5'-GAG TCAT TCT CGA CTT GCG GCC GCA CGT TTG ATC/T TCC AC/GC TTG GTC CC-3';

$V_H$4 SfiI/NcoI:
(SEQ ID NO:17)
5'-GTC CTC GCA ACT GCG GCC CAG CCG GCC ATG GCC CAG GTG CAG CTG CA/GG AGT CGG G-3';

$V_H$6 SfiI/NcoI:
(SEQ ID NO:18)

```
-continued
5'-GTC CTC GCA ACT GCG GCC CAG CCG GCC ATG GCC CAG
GTA CAG CTG CA/GC AGT CAG G-3';

J_H3 SalI:
                                           (SEQ ID NO:19)
5'-GAG TCA TTC TCG TGT CGA CAC GGT GAC CAT TGT
CCC-3';

J_H2 SalI:
                                           (SEQ ID NO:20)
5'-GAG TCA TTC TCG TGT CGA CAC AGT GAC CAG GGT
GCC-3';

mGuy13 ApaLI:
                                           (SEQ ID NO:21)
5'-TGA GCA CAC AGT GCA CTC GAC ATC GAG CTC ACT CAG
TCT CC-3';

mGuy13 NotI:
                                           (SEQ ID NO:22)
5'-TTT TCC TTT TGC GGC CGC CCG TTT TAT TTC CAA CTT
TGT-3';
and mGuy13 SalI:
                                           (SEQ ID NO:23)
5'-GAG TCA TTC TCG TGT CGA CAC GGT GAC CGT GGT GCC
TTG GCC CCA GTA GTC AAA GTA GGT-3'.
```

EXAMPLE 9

Large-Scale Recombinant Protein Production

Recombinant proteins were recovered from the bacterial periplasm following induction with 0.5 mM final concentration of IPTG for 3-4 hours at 30° C. (Breitling, et al (1991) *Gene* 104:147-153). After centrifugation (4000×g, 4° C., 30 minutes), the pellet was resuspended in 10 mL 30 mM Tris-HCl (pH 8.2) containing 20% sucrose, 1 mM EDTA, incubated on ice for 15 minutes and centrifuged as above. The pellet was resuspended in 10 mL 5 mM MgSO$_4$, 1 mM EDTA and incubated for 15 minutes on ice before a final centrifugation step as above. Both supernatants were pooled, dialyzed against PBS and stored at 4° C. Recombinant proteins were also expressed in the periplasm under osmotic stress in the presence of compatible solutes (Barth, et al. (2000) *Appl. Environ. Microbiol.* 66:1572-9). Briefly, bacteria were grown overnight at 26° C. in Terrific Broth (TB) (12 gram/L bactotryptone, 24 gram/L bacto-yeast-extract, 4 mL/L glycerol) containing 100 µg/mL ampicillin and 0.5 mM ZnCl$_2$. The culture was diluted 30-fold in 200 mL of the same medium. When the OD$_{600}$ nm of the culture reached 2.0, it was supplemented with 0.5 M sorbitol, 4% NaCl, 40 mM glycine betaine and incubated at 26° C. for an additional 30-60 minutes. Expression was induced with 1 mM final concentration IPTG and growth for 6 hours at 26° C. Cells were harvested by centrifugation at 30,000×g for 10 minutes. The recombinant antibody fragments were isolated from the periplasmic space as described above. The periplasmic and osmotic shock fractions were pooled and dialyzed against PBS. Phenylmethylsuphonylfluoride (PMSF) was added to a final concentration of 1 mM.

EXAMPLE 10

Purification of Recombinant Proteins

The human scFv and diabody antibody fragments were purified by IMAC using the His6 tag in accordance with well-known methods (Griffiths, et al. (1994) EMBO J. 13:3245-3260). Briefly, 10 mL columns (BIO-RAD Polyprep chromatography columns) were packed with 500 µL Ni-NTA resin (Qiagen) and washed with five column volumes of PBS prior to loading with the recombinant proteins. The columns were washed with 10 column volumes of PBS containing 10 mM imidazol. Bound proteins were eluted with 250 mM imidazol and collected in 1 mL fractions. Protein concentrations were determined by spectrophotometry assuming that A 280 nm=1 corresponds to a scFv or diabody concentration of 0.7 mg/mL. Gel filtration was used for further purification. A SEPHADEX 200 column (Pharmacia) was equilibrated with PBS. ScFv or diabody antibody fragments were loaded and run at 1 mL/minute. Aprotinin (6500 Da), cytochrome C (12,400 Da), carbonic anhydrase (29,000 Da), BSA (66,000 Da) and Dextran Blue (2,000,000 Da) were used as molecular weight standards (Fluka, Buchs, Switzerland).

EXAMPLE 11

Enzyme-Linked Immunosorbent Assay (ELISA)

*Streptococcus mutans*, SAI/II antigen or bovine serum albumin (BSA) were coated on ELISA plates (Nalge Nunc International, Rochester, N.Y.) at a concentration of 1-10 µg per well in PBS overnight at 4° C. The plates were washed three times with PBS and blocked with 2% milk powder in PBS for 2 hours at room temperature. The scFvs were tested either at a concentration of 1 µg per well or 100 µL per well of overnight-induced culture. Recombinant antibodies containing the MYC tag were detected with the murine 9E10 monoclonal antibody (ATCC CRL1729). Antibodies containing a H is 6 tag were detected using the murine anti-Penta-HIS antibody (Qiagen). The murine antibodies were detected with a goat-anti-mouse (Fc-specific) peroxidase-labeled antibody. The assays were developed with 3,3',5,5'-tetramethylbenzidine (TMB) (Sigma, St. Louis, Mo.). Reactions were stopped by the addition of H$_2$SO$_4$ after 20 minutes and readings taken at OD$_{450}$ nm. Between every incubation step, the plates were washed three times with PBS/0.05% TWEEN 20 and three times with PBS.

EXAMPLE 12

Aggregation of *Streptococcus mutans*

Cultured *Streptococcus mutans* was divided into 20-µL aliquots and incubated with serial dilutions of bacterially expressed recombinant antibodies for 2 days at 4° C. or 1 hour at 37° C. on Lab-Tek II chamber slides (Nalge Nunc International). Excess medium was discarded and the cells were air-dried. The bacteria were counterstained with Gram solution (Diagnostica Merck, Darmstadt, Germany). The slides were mounted with Immunofluor medium (ICN Biomedicals, Inc., Costa Mesa, Calif.) and photographed with a Zeiss Axioskob immunofluorescence microscope.

What is claimed is:

1. A vector comprising a nucleic acid sequence encoding a diabody which specifically binds *Streptococcus* Surface Antigen I/II, wherein the diabody comprises a human heavy chain variable domain having the amino acid sequence of SEQ ID NO:3, SEQ ID NO:5, or SEQ ID NO:7; or a human light chain variable domain having the amino acid sequence of SEQ ID NO:4, SEQ ID NO:6, or SEQ ID NO:8.

2. An isolated host cell comprising a vector of claim 1.

* * * * *